US012653512B2

(12) United States Patent
Cheng et al.

(10) Patent No.: US 12,653,512 B2
(45) Date of Patent: Jun. 16, 2026

(54) PROSTATE PUNCTURE GUIDANCE METHOD, APPARATUS, DEVICE AND SYSTEM BASED ON MULTI-MODAL FUSION

(71) Applicant: Carbon (Shenzhen) Medical Device Co, Ltd., Shenzhen (CN)

(72) Inventors: Fan Cheng, Shenzhen (CN); Shanshan Wang, Shenzhen (CN); Yuan Ruan, Shenzhen (CN); Xiongwen Huang, Shenzhen (CN)

(73) Assignee: Carbon (Shenzhen) Medical Device Co., Ltd., Shenzhen (CN)

( * ) Notice: Subject to any disclaimer, the term of this patent is extended or adjusted under 35 U.S.C. 154(b) by 0 days.

(21) Appl. No.: 19/173,862

(22) Filed: Apr. 9, 2025

(65) Prior Publication Data

US 2025/0318814 A1 Oct. 16, 2025

(30) Foreign Application Priority Data

Apr. 12, 2024 (CN) ......................... 202410438311.X

(51) Int. Cl.
*A61B 10/02* (2006.01)
*A61B 34/10* (2016.01)
(Continued)

(52) U.S. Cl.
CPC .......... *A61B 10/0241* (2013.01); *A61B 34/10* (2016.02); *G06T 11/60* (2013.01); *A61B 2034/2051* (2016.02); *A61B 2034/2063* (2016.02); *A61B 2034/2065* (2016.02); *G06T 2210/41* (2013.01)

(58) Field of Classification Search
None
See application file for complete search history.

(56) References Cited

U.S. PATENT DOCUMENTS 10,092,773 B2 * 10/2018 Leong .................... A61N 5/103
2004/0225174 A1 * 11/2004 Fuller .................... G16H 30/40
702/19

(Continued)

OTHER PUBLICATIONS

The Extended European Search Report Issued on Sep. 3, 2025 for Corresponding European Patent Application No. 25168454.4.

*Primary Examiner* — Patricia J Park

(57) ABSTRACT

Disclosed are a prostate puncture guidance method, apparatus, device and system based on multi-modal fusion. The prostate model of the object to be examined and the ultrasonic probe model with at least one scanning plane are displayed in the same display area. Based on the real-time coordinate and ultrasound image information collected by the ultrasonic probe, the display area dynamically displays dynamic updates. Users may get the positional relationship between at least one scanning plane and the target identifier in the prostate model. This allows for quickly and accurately understanding the intersection between the scanning plane corresponding to the puncture plate installed on the ultrasonic probe and the target identifier. Additionally, through another display area showing the correlation between the specific puncture hole in the puncture plate and the target identifier, sampling can be quickly completed through the sampling device by penetrating the specific puncture hole.

16 Claims, 9 Drawing Sheets

(51) Int. Cl.
  _G06T 11/60_          (2006.01)
  _A61B 34/20_          (2016.01)

(56)          References Cited

U.S. PATENT DOCUMENTS

2010/0016710 A1 *   1/2010   Kumar ..................... A61B 8/12
                                                        600/425
2011/0009748 A1 *   1/2011   Greene ................... A61B 8/08
                                                        600/443
2012/0184851 A1     7/2012   Arai et al.
2021/0251696 A1 *   8/2021   Krueckers ................ G06T 7/37
2022/0133284 A1 *   5/2022   Lampotang ........ A61B 10/0241
                                                        600/562
2024/0115322 A1     4/2024   Huang et al.

* cited by examiner

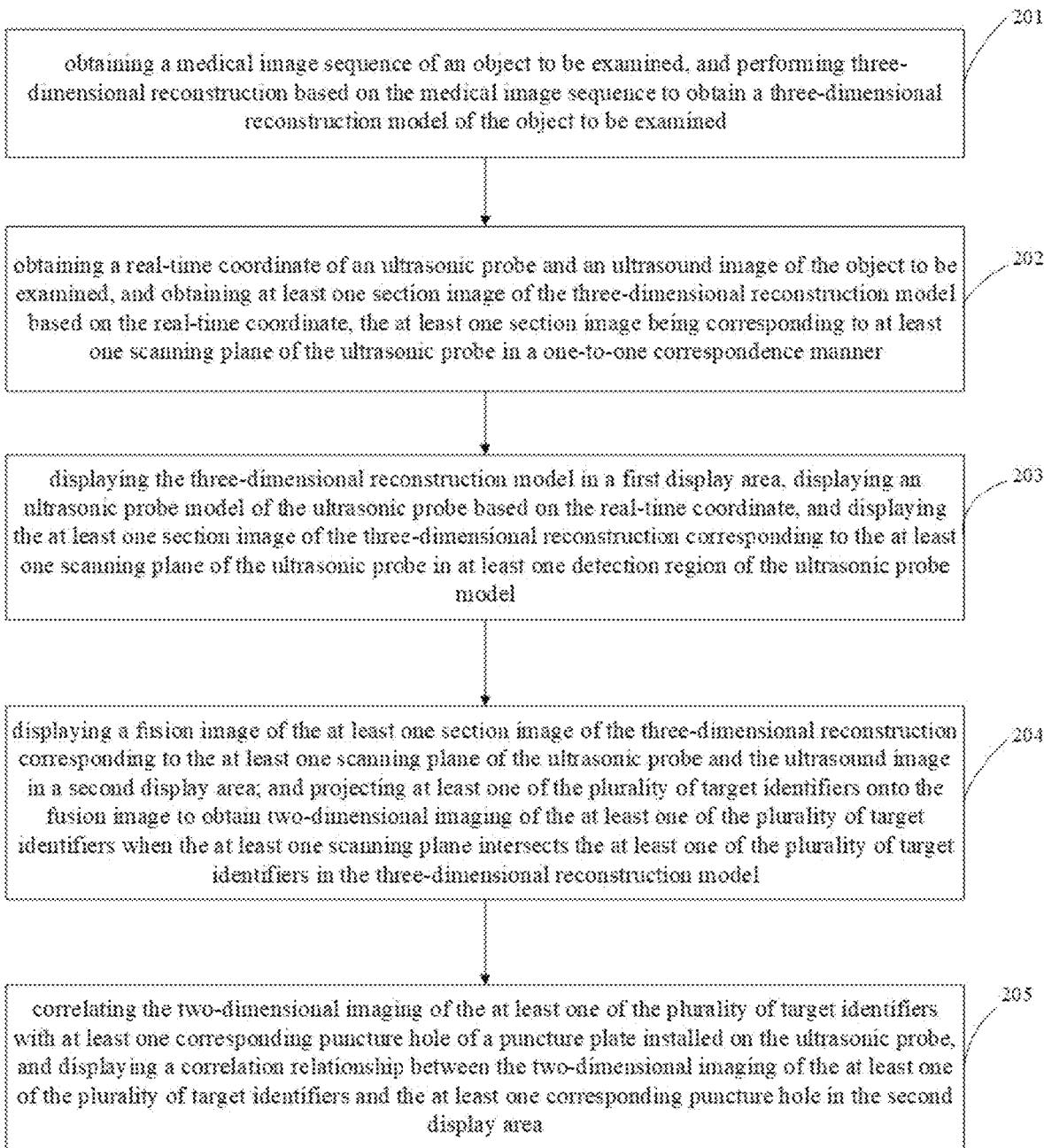

201 obtaining a medical image sequence of an object to be examined, and performing three-dimensional reconstruction based on the medical image sequence to obtain a three-dimensional reconstruction model of the object to be examined

202 obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner

203 displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model

204 displaying a fusion image of the at least one section image of the three-dimensional reconstruction corresponding to the at least one scanning plane of the ultrasonic probe and the ultrasound image in a second display area; and projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model

205 correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area

FIG. 2

PROSTATE PUNCTURE GUIDANCE METHOD, APPARATUS, DEVICE AND SYSTEM BASED ON MULTI-MODAL FUSION

CROSS-REFERENCE TO RELATED APPLICATIONS

The present disclosure claims priority of Chinese Patent Application No. 202410438311.X, filed on Apr. 12, 2024, the entire contents of which are hereby incorporated by reference.

TECHNICAL FIELD

The present disclosure relates to the technical fields of medical devices and prostate puncturing, and in particular to a prostate puncture guidance method, apparatus, device and system based on multi-modal fusion.

BACKGROUND

Prostate biopsy is a procedure to obtain prostate tissues through puncture for pathological examination, which is of great significance in the clinical practice, in particular to the confirmation of prostate cancer.

As for the typical puncture guidance systems, the position of the biopsy needle is generally obtained through position sensors, and the position of the needle tip in ultrasound or fusion image is predicted based on the relevant algorithms. When the imaging quality of the needle tip is poor, the display status of the needle tip is highlighted by enhancing the displaying or using special markers to help users to accurately track the position of the needle tip. However, to ensure comprehensive sampling, multiple punctures are typically required for prostate biopsy. Under current technological conditions, if the doctors are inexperienced or the patients are intolerant to pain and have relative short durations of anesthesia, the patients may suffer during the puncture process due to long procedure time periods, and repeated punctures caused by low precision, which may even lead to failure to successfully complete the surgery. These issues further increase the operational difficulty for medical staff, lengthen their learning time, and impact the overall surgical experience for patients.

SUMMARY

Based on this, it is necessary to provide a prostate puncture guidance method, apparatus, device and system based on multi-modal fusion to overcome or at least alleviate the problems in the prior art, such as prolonged puncture time, low puncture accuracy leading to repeated punctures, and poor patient surgical experience.

According to a first aspect, the present disclosure provides a prostate puncture guidance method based on multi-modal fusion, including:

obtaining a medical image sequence of an object to be examined, and performing three-dimensional reconstruction based on the medical image sequence to obtain a three-dimensional reconstruction model of the object to be examined, wherein the three-dimensional reconstruction model includes a prostate structure of the object to be examined, the prostate structure includes a plurality of target identifiers, and the plurality of target identifiers include at least one of a prostate puncture marker and a target area marker;

obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner;

displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model;

displaying a fusion image of the at least one section image of the three-dimensional reconstruction corresponding to the at least one scanning plane of the ultrasonic probe and the ultrasound image in a second display area;

projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area.

In some embodiments, the step of projecting at least one of the plurality of target identifiers onto the fusion image to obtain two-dimensional imaging of the at least one of the plurality of target identifiers includes:

acquiring first coordinate information of the at least one scanning plane and second coordinate information of the at least one of the plurality of target identifiers that intersects the at least one scanning plane; and projecting the at least one of the plurality of target identifiers onto the fusion image of the at least one scanning plane in two dimensions based on the first coordinate information and the second coordinate information.

In some embodiments, the method further includes generating at least one prostate puncture marker within a two-dimensional projection of the target area marker in the fusion image.

In some embodiments, the method further includes in response to a first operation, acquiring at least one target identifier selected by the first operation, that is followed by highlighting the at least one target identifier in the first display area; and/or hiding the at least one target identifier in the second display area.

In some embodiments, the method further includes displaying the at least one section image of the three-dimensional reconstruction corresponding to the at least one scanning plane in respective sub-display areas of a third display area.

In some embodiments, the method further includes in response to a needle tip enhancement command, displaying at least one of a needle tip position of a sampling device and a safe puncture area in the fusion image based on a real-time coordinate of the sampling device.

In some embodiments, the method further includes displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters include at least one of contrast and transparency, and the identification parameters include outline colors.

According to a second aspect, the present disclosure provides a prostate puncture guidance apparatus based on multi-modal fusion, including: a three-dimensional reconstruction module, configured for obtaining a medical image sequence of an object to be examined, and performing three-dimensional reconstruction based on the medical image sequence to obtain a three-dimensional reconstruction model of the object to be examined, wherein the three-dimensional reconstruction model includes a prostate structure of the object to be examined, the prostate structure includes a plurality of target identifiers, and the plurality of target identifiers include at least one of a prostate puncture marker and a target area marker;

an ultrasound data acquisition module, configured for obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner;

a model display module, configured for displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model;

a fusion image display module, configured for displaying a fusion image of the at least one section image of the three-dimensional reconstruction corresponding to the at least one scanning plane of the ultrasonic probe and the ultrasound image in a second display area; and projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and a puncture correlation module, configured for correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area.

In some embodiments, the fusion image display module is further configured for:

acquiring first coordinate information of the at least one scanning plane and second coordinate information of the at least one of the plurality of target identifiers that intersects the at least one scanning plane; and projecting the at least one of the plurality of target identifiers onto the fusion image of the at least one scanning plane in two dimensions based on the first coordinate information and the second coordinate information.

In some embodiments, the apparatus is further configured for generating at least one prostate puncture marker within a two-dimensional projection of the target area marker in the fusion image.

In some embodiments, the apparatus is further configured for in response to a first operation, acquiring at least one target identifier selected by the first operation, that is followed by highlighting the at least one target identifier in the first display area; and/or hiding the at least one target identifier in the second display area.

In some embodiments, the apparatus is further configured for displaying the at least one section image of the three-dimensional reconstruction corresponding to the at least one scanning plane in respective sub-display areas of a third display area.

In some embodiments, the apparatus is further configured for displaying at least one of a needle tip position of a sampling device and a safe puncture area in the fusion image based on a real-time coordinate of the sampling device, in response to a needle tip enhancement command.

In some embodiments, the apparatus is further configured for displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters include at least one of contrast and transparency, and the identification parameters include outline colors.

According to a third aspect, the present disclosure provides a computer device, including a memory and a processor. The memory stores a computer program, and when the computer program is executed by the processor, the method according to the first aspect is implemented.

According to a fourth aspect, the present disclosure provides a prostate puncture guidance system based on multi-modal fusion, including the above-mentioned computer device, a magnetic field generator, a first electromagnetic sensor, a second electromagnetic sensor, an ultrasonic probe, a puncture plate, a sampling device and a display terminal. The ultrasonic probe is equipped with the puncture plate, the ultrasonic probe is provided with the first electromagnetic sensor, the sampling device is provided with the second electromagnetic sensor, and the magnetic field generator, the display terminal, the ultrasonic probe and the electromagnetic sensors are respectively in communication connection with the computer device.

In the embodiments of the present disclosure, the prostate model of the object to be examined and the ultrasonic probe model with at least one scanning plane are displayed in the same display area. Based on the real-time coordinate and ultrasound image information collected by the ultrasonic probe, the display area dynamically displays dynamic updates. Users may get the positional relationship between at least one scanning plane and the target identifier in the prostate model. This allows for quickly and accurately understanding the intersection between the scanning plane corresponding to the puncture plate installed on the ultrasonic probe and the target identifier. Additionally, through another display area showing the correlation between the specific puncture hole in the puncture plate and the target identifier, sampling can be quickly completed through the sampling device by penetrating the specific puncture hole. This reduces sampling time, decreases the number of punctures, avoids repeated punctures, lowers the operational level and learning time for medical staff, and enhances the surgical experience of patients.

BRIEF DESCRIPTION OF DRAWINGS

FIG. 2 is a flow chart of a prostate puncture guidance method according to an embodiment of the present disclosure;

DESCRIPTION OF EMBODIMENTS

Figure 1:
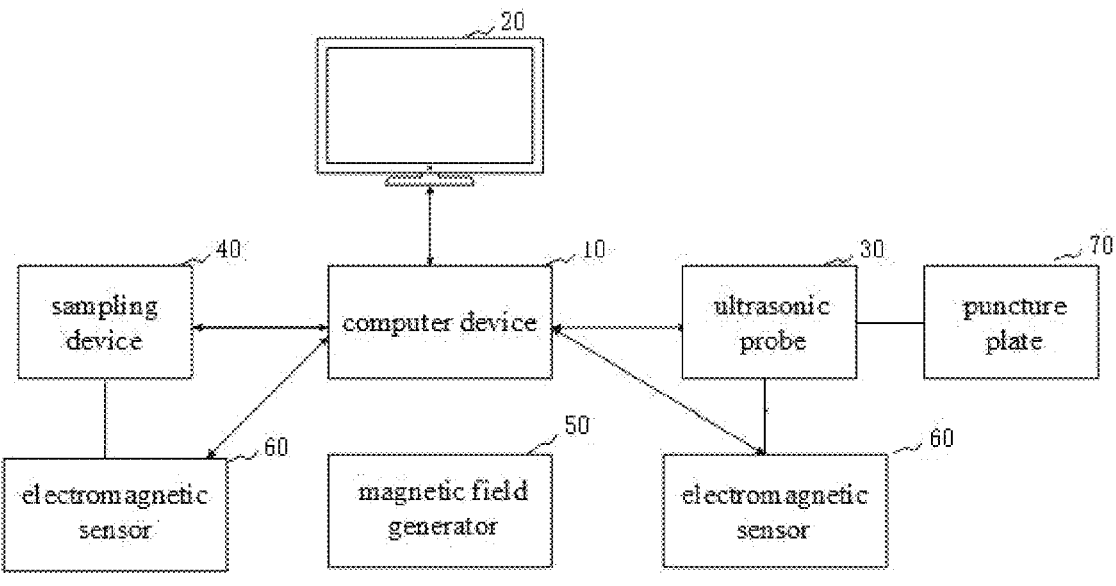
FIG. 1 is a schematic structural view of a prostate puncture guidance system according to an embodiment of the present disclosure.

In order to make the objectives, technical solutions, and advantages of the present disclosure apparent, the following detailed description is provided in conjunction with the accompanying drawings and embodiments. It should be understood that the specific embodiments described here are intended to explain the present disclosure and are not meant to limit it.

The terms "include," "comprise," "have," and any variations thereof used in the present disclosure are intended to cover non-exclusive inclusion, meaning that for example a process, method, system, product, or device that includes a series of steps or units is not limited to the steps or units explicitly described but may also include other steps or units that are not explicitly described or inherent to the process, method, product, or device.

Unless otherwise explicitly specified, the term "multiple"/ "a/the plurality of" as used in the present disclosure means two or more (including two).

The terms "first," "second," etc., are used to distinguish similar objects by naming, but these objects are not limited by the terms. The terms should not be understood as indicating or implying relative importance or implicitly specifying the number, specific order, or hierarchical relationship of the technical features referred to. It should be understood that, without departing from the scope of the present disclosure, these terms can be interchangeable where appropriate. For example, "first sub-region" may be described as "second sub-region," and similarly, "second sub-region" may be described as "first sub-region."

The following industry terms are used in the context:

Multi-modal fusion or ultrasound fusion referring to a technology that combines ultrasound (US) images with cross-sectional images from computed tomography (CT), nuclear magnetic resonance imaging (MRI), or positron emission tomography (PET) and synchronously displays them in real-time on the same screen. In this technology, CT, MRI, or PET images are input into the ultrasound system, the ultrasound images are registered with the CT, MRI, or PET cross-sectional images using various localization methods, and the real-time linkage between ultrasound images and volumetric images of CT, MRI, or PET is achieved by using magnetic field localization. It has characteristics of high resolution of CT, MRI, or PET images with the real-time nature, ease of operation, and arbitrary cross-sectional display of ultrasound images, thereby supplementing various imaging information to accurately locate lesional positions.

CT as a versatile diagnostic tool, may realize a cross-sectional scan of the body. It may also refer to electronic computer X-ray tomography technology. CT performs examination to the human body by measuring the various absorption and transmission of X-rays by different body tissues with highly sensitive instruments. The obtained data is transferred to a computer and the computer processes the data to produce sectional or three-dimensional images of the examined body parts, allowing detection of small lesions in the body. CT is commonly used to examine the chests and abdomens of cancer patients. The chest CT has superior sensitivity and accuracy in detecting chest lesions compared to regular X-ray chest films, especially for the diagnosis of early-stage lung cancers, chest CT plays a decisive role. However, CT uses X-rays, which causes certain radiation exposure to the human body, and it provides insufficient resolution for soft tissues imaging.

MRI, i.e., nuclear magnetic resonance imaging, differentiates tissue characteristics mainly based on hydrogen content in the body, thereby assessing organ functions and identifying lesions. MRI is primarily used to diagnose diseases of central nervous system, and assessing injures to soft tissues and ligaments, such as diagnosis of meningiomas, gliomas, astrocytomas, as well as cartilage and ligament tears.

Cross-section view, sectional view or section view: CT, MRI, or PET generate cross-sectional images of the body at fixed angles. With reference to the body anatomy, sections are divided into sagittal plane (sag), coronal plane (cor), and transverse plane (tra):

Sagittal plane divides the body into left and right parts wherein the left cross section and the right cross section are sagittal planes, and the sagittal plane are called as the mid-sagittal plane where the left and right halves are equal.

Coronal plane vertically divides the body into anterior and posterior parts along the left-to-right direction.

Transverse plane transects the body horizontally along a plane parallel to the ground, dividing the body into upper and lower parts.

The term "and/or" used in the present disclosure is simply a way to describe the relationship between related objects, indicating that there may be three options. For example, the expression A and/or B can represent any one of the following cases: A alone, both A and B together, or B alone.

To make the objectives and advantages of the present disclosure more apparent, a detailed explanation of the issues identified in the prior art is provided.

Prostate biopsy is a procedure to obtain prostate tissues through puncture for pathological examination, which is of great significance in the clinical practice of prostate cancer. The mainstream puncture methods in the clinical practice include transrectal puncture and transperineal puncture, each with its own advantages and disadvantages. However, no matter which method is used, in order to ensure comprehensive sampling, the puncturing sampling points need to completely cover the prostate. Typically, the prostate biopsy requires 10 to 12 cores at different locations of the prostate. This large number of punctures requires precise anesthesia to locate the anesthesia zone accurately and select the appropriate length of anesthesia needles. In addition, the sampling time should be as short as possible. If anesthesia is ineffective, the operation duration for puncture is too long, there are repeated punctures caused by low puncture precision or difficulties in distinguishing previously punctured areas it makes the procedure extremely painful for the patient and can even lead to failure to successfully complete the surgery.

To solve or at least alleviate the above problems, the present disclosure provides a prostate puncture guidance method, apparatus, device and system based on multi-modal fusion. The prostate model of the object to be examined and the ultrasonic probe model with at least one scanning plane are displayed in the same display area. Based on the real-time coordinate and ultrasound image information collected by the ultrasonic probe, the display area dynamically displays dynamic updates. Users may get the positional relationship between at least one scanning plane and the target identifier in the prostate model. This allows for quickly and accurately understanding the intersection between the scanning plane corresponding to the puncture plate installed on the ultrasonic probe and the target identifier. Additionally, through another display area showing the correlation between the specific puncture hole in the puncture plate and the target identifier, sampling can be quickly completed through the sampling device by penetrating the specific puncture hole. This reduces sampling time, decreases the number of punctures, avoids repeated punctures, lowers operation level and learning time for medical staff, and enhances the surgical experience of patients.

As shown in FIG. 1, the prostate puncture guidance system based on multi-modal fusion provided in the present disclosure includes a computer device 10, a display terminal 20, an ultrasonic probe 30, a sampling device 40, a magnetic field generator 50, electromagnetic sensors 60, and a puncture plate 70. The magnetic field generator 50 is arranged in a fixed position in the application environment. Usually, the magnetic field generator 50 can work independently with a power supply, or can be powered through the supply to the computer device 10, which has a built-in control module that controls the power supply and switches signals to the magnetic field generator 50. The ultrasonic probe 30 is equipped with a first electromagnetic sensor, the sampling device 40 is equipped with a second electromagnetic sensor, and the ultrasonic probe 30 is fixedly mounted with the puncture plate 70. Each electromagnetic sensor 60 is used to sense the magnetic field to determine the three-dimensional coordinate and directional information within the magnetic field provided by the magnetic field generator 50. The coordinate and information are then transmitted back to the computer device 10 through communication connection. The computer device 10 obtains the coordinate information of the ultrasonic probe 30 and the sampling device 40 under the coordinates system magnetic field generator 50. The display terminal 20, the ultrasonic probe 30, and the sampling device 40 are all in communication connection with the computer device 10.

The computer device 10 is configured for obtaining a medical image sequence of an object to be examined, and performing three-dimensional reconstruction based on the medical image sequence to obtain a three-dimensional reconstruction model of the object to be examined, wherein the three-dimensional reconstruction model comprises a prostate structure of the object to be examined, the prostate structure comprises a plurality of target identifiers, and the plurality of target identifiers comprise at least one of a prostate puncture marker and a target area marker; obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner; displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model; displaying a fusion image of the at least one section image of the three-dimensional reconstruction corresponding to the at least one scanning plane of the ultrasonic probe and the ultrasound image in a second display area; projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area.

In the present disclosure, the prostate model of the object to be examined and the ultrasonic probe model with at least one scanning plane are displayed in the same display area. Based on the real-time coordinate and ultrasound image information collected by the ultrasonic probe, the display area dynamically displays dynamic updates. Users may get the positional relationship between at least one scanning plane and the target identifier in the prostate model. This allows for quickly and accurately understanding the intersection between the scanning plane corresponding to the puncture plate installed on the ultrasonic probe and the target identifier. Additionally, through another display area showing the correlation between the specific puncture hole in the puncture plate and the target identifier, sampling can be quickly completed through the sampling device by penetrating the specific puncture hole. This reduces sampling time, decreases the number of punctures, avoids repeated punctures, lowers the operational level and learning time for medical staff, and enhances the surgical experience of patients.

It should be understood that although the steps in the flow chart of FIG. 2 are listed in sequence with the arrows, these steps are not necessarily executed in the order indicated by the arrows. Unless explicitly stated in this document, the execution order of these steps is not strictly limited, and these steps may be performed in a different order. Additionally, at least some of the steps in FIG. 2 may include multiple sub-steps or stages, which do not necessarily need to be completed simultaneously but may be executed at different times. The execution order of these sub-steps or stages does not have to follow a strict sequence and may be executed with other steps or sub-steps or stages of other steps alternately.

FIG. 2 is a flow chart of a prostate puncture guidance method based on multi-modal fusion according to an embodiment of the present disclosure. This method can be executed by a prostate puncture guidance apparatus based on multi-modal fusion, which can be implemented through software and/or hardware. This software and/or hardware is generally integrated into electronic equipment. The integration can be in the form of a client being installed on the corresponding electronic device. This client can be an application for displaying the puncture guidance interface, a web-based client, or a sub-application running within the operating environment of a main application. The electronic device can include personal computers, laptops, smartphones, tablet computers, smartwatches, and personal digital assistants (PDAs), among other mobile devices. It can also include desktop computers and other devices. Further, it can be medical equipment such as ultrasound fusion devices.

In the following embodiments, each embodiment also provides optional features and examples. The various features recorded in the embodiments can be combined to form multiple optional solutions, and each numbered embodiment should not be viewed as a single technical solution.

In one embodiment, as shown in FIG. 2, a prostate puncture guidance method based on multi-modal fusion is provided, which includes the following Steps 201 to 205.

Step 201: obtaining a medical image sequence of an object to be examined, and performing three-dimensional reconstruction based on the medical image sequence to obtain a three-dimensional reconstruction model of the object to be examined, wherein the three-dimensional reconstruction model comprises a prostate structure of the object to be examined, the prostate structure comprises a plurality of target identifiers, and the plurality of target identifiers comprise at least one of a prostate puncture marker and a target area marker The medical image refers to an image obtained using medical imaging technology, which contains information about the internal human anatomy. In one embodiment, medical images include but are not limited to CT images, MRI images, and PET images. Compared to ultrasound image, CT and MRI may provide multi-dimensional 3D section image, which helps doctors gain a more comprehensive understanding of the location and morphology of lesions, enabling more accurate diagnoses.

The medical images contain anatomy information about the patient prostate. In one embodiment, the user imports the medical image sequence of the patient through a computer device. The computer device then performs three-dimensional reconstruction based on the medical image sequence to obtain the three-dimensional reconstruction model of the patient. This three-dimensional reconstruction model includes the prostate anatomy of the patient. After performing the three-dimensional reconstruction, the model accurately reflects the actual condition of the prostate of the object to be examined, making it easier for medical staff to perform accurate punctures and sampling.

Specifically, the step of obtaining a medical image sequence of an object to be examined, and performing three-dimensional reconstruction based on the medical image sequence to obtain a three-dimensional reconstruction model of the object to be examined may include a plurality of steps. To make it more convenient for users to perform the aforementioned steps, each step can be provided with an operation interface, allowing users to follow the guidance on the interface to operate each step. In one embodiment, the following steps may be included:

1. importing a medical image sequence: the user imports the medical image sequence through an import operation interface;
2. locating prostate: the user determines the location of the prostate through a provided prostate locating interface;
3. determining a first frame of the prostate;
4. determine the last frame of the prostate: the user filters out the first and last frames of the prostate from the imported medical image sequence by confirming the first and last frames through a confirmation interface;
5. prostate segmentation confirmation: in response to the first and last frame confirmation commands, the computer device displays the prostate segmentation interface, through which the user confirms the position of the prostate;
6. lesion target confirmation: according to the prostate segmentation confirmation command, the computer device switches to the target confirmation interface. In this interface, the user can selectively add targets. These targets are the suspected lesion locations, which assist doctors in performing punctures more quickly and effectively, reducing sampling time and the incidence of complications;
7. three-dimensional reconstruction: in response to the lesion target confirmation operation, the computer device performs three-dimensional reconstruction based on the confirmed image sequence and the positioning information of the patient during medical imaging, to obtain a three-dimensional reconstruction model;
8. systemic needle planning: in response to the three-dimensional reconstruction model confirmation command, the computer device switches to the interface of systemic needle planning. In this interface, the user can select the default layout of 12 cores, or add additional cores. After confirming the final number and layout of the cores, the computer device extracts the image sequence with the largest cross-sectional area from the medical image sequence as the projection object. Using local deformation techniques, the core layout is projected onto this image sequence. Then, based on the position and pixel information of each core on the sequence image, a two-dimensional to three-dimensional transformation is performed to generate a plurality of irregular ellipsoid-shaped prostate puncture markers of different volumes and different positions in the prostate structure of the three-dimensional reconstruction model. The number of the prostate puncture markers is corresponding to the number of the cores.

The target identifier is used to mark the region of interest in the prostate structure. The prostate puncture marker can be generated according to the detailed explanation of step 8 (systemic needle planning) above and will not be repeated here. For the target area marker, reference can be made to step 6 (lesion target confirmation). The target area marker may be the suspected lesion area outlined by the user, alternatively, it may be any other region of interest outlined by the user. The generation principle of the target area marker in the prostate structure is similar to the generation principle of core positions in step 8. After selecting one or more target areas from part or all of the image sequences, a plurality of irregular ellipsoid-shaped target area markers of different volumes and different positions can be generated in the prostate structure of the three-dimensional reconstruction model through a two-dimensional to three-dimensional transformation. The number of the prostate puncture markers is corresponding to the number of the cores.

In an implementation scenario, after the CT, MRI, or PET image data of the object to be examined has been imported and the prostate puncture markers have been drawn by the user, it comes to the prostate puncture guidance step. A three-dimensional prostate model based on the previously acquired CT, MRI, or PET image data (used as the reconstruction foundation) is displayed in a display area or the full screen of the display device or monitor. This model is also provided with a plurality of prostate puncture markers drawn earlier which are distributed therein. The distribution regions and positions are determined by the target identifiers drawn previously.

In one embodiment, the prostate puncture markers are determined by the system puncture template, with the number of puncture needles being twelve.

Step 202: obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner.

The real-time coordinate of the ultrasonic probe is obtained through an electromagnetic sensor mounted on the ultrasonic probe by positioning in the electromagnetic coordinate system generated by a magnetic field generator.

Section image refers to one image in the medical image sequence of the object to be examined obtained in the previous text.

The principle of obtaining the section image in the three-dimensional reconstruction model corresponding to the scanning plan by acquiring the real-time coordinate of the ultrasonic probe is as follows:

Medical image sequence such as CT, MRI, or PET image sequence that includes images acquired by an image acquisition device based on the respective coordinate system provided. Each image in the sequence has a corresponding coordinate information. Since the electromagnetic coordinate system used for ultrasound image is inconsistent with the coordinate systems provided by other imaging devices, it is necessary to perform registering of the two coordinate systems. The method includes the following operations.

The ultrasound image sequence is obtained. The computer device receives the ultrasound sequence images of the human body, extracts the three-dimensional coordinates of the four vertices of each ultrasound image frame, and reconstructs the ultrasound volume data. Simultaneously, an ICP iterative algorithm is used to perform three-dimensional registering between the reconstructed ultrasound volume data and the three-dimensional reconstruction model, thereby obtaining the registration transformation coefficients. These transformation coefficients are used to convert the three-dimensional coordinates corresponding to the ultrasound data into the three-dimensional coordinate system of the medical image data.

Once the coordinate systems are registered, the user can use the ultrasonic probe to acquire real-time ultrasound image from each scanning plane. The computer device, using the electromagnetic sensor, obtains the real-time coordinates of each scanning plane in the electromagnetic coordinate system. Based on the real-time coordinates and the registration transformation coefficients, the computer obtains the intersection position of each scanning plane in the three-dimensional model. The model is then sliced according to the intersection position of each scanning plane in the three-dimensional model to obtain the MRI image cross-section corresponding to each scanning plane. Taking MRI as an example, intersection image refers to the MRI transverse section of the probe scanning plane of the current ultrasonic probe in the three-dimensional reconstruction model.

Step 203: displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model.

In the first display area, the three-dimensional reconstruction model with the prostate structure is displayed. The display position can be centered in the display area or set to another position based on the user preferences.

Based on the real-time coordinate of the ultrasonic probe acquired from the electromagnetic sensor, the ultrasonic probe model is displayed in the same spatial system as the three-dimensional reconstruction model in the first display area. The display position is determined by the real-time coordinate, allowing users to quickly and accurately understand the spatial relationship between the ultrasonic probe and the prostate. Additionally, a plurality of detection regions of the probe are shown on the ultrasonic probe model to represent the real scanning areas of the probe. Corresponding section image is displayed synchronously on each scanning plane. Taking MRI as an example, the MRI transverse sections of the scanning planes are displayed synchronously in the three-dimensional reconstruction model.

The first display area can be the full-screen display area of an independent display device, a certain display area in a partitioned display, or a full-screen display area or a partitioned display area on a computer device with a monitor. It can also be the entire display area or a partitioned display area on a user web page or integrated computer device.

Step 204: displaying a fusion image of the at least one section image of the three-dimensional reconstruction corresponding to the at least one scanning plane of the ultrasonic probe and the ultrasound image in a second display area; and projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model.

Fusion image refers to the fusion of ultrasound image acquired in real-time by the ultrasonic probe and a section image in the medical image sequence (such as CT, MRI, or PET image sequence). The type of the section image to be fused is determined by the type of medical image sequence imported in Step 201. Based on the real-time coordinate of the ultrasonic probe, the corresponding section image is obtained from the three-dimensional reconstruction model. The organ contours, previously outlined, are used as the registration target. For instance, in the case of MRI images of the prostate, both the ultrasound image and MRI images outline or automatically identify the corresponding contours of the prostate. The ultrasound image and MRI image are then registered and overlapped based on the prostate contour, so both images are displayed on the same display area to obtain fusion image of different images.

Similarly, based on the coordinate information of the scanning plane and the coordinate information of the target identifier, the transection projection of the target identifier, i.e., the two-dimensional imaging of the target identifier, onto the scanning plane is calculated. Since it is the ultrasound image that is acquired from the scanning plane, that is to say, the two-dimensional imaging of the target identifier onto the scanning plan is two-dimensional imaging of the target identifier on the ultrasound image. Since the ultrasound image and the section image are accurately fused based on the organ contours, the two-dimensional image of the target identifier displayed on the ultrasound image can be accurately and synchronically displayed on the corresponding fusion image.

Step 205: correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area.

Figure 3:
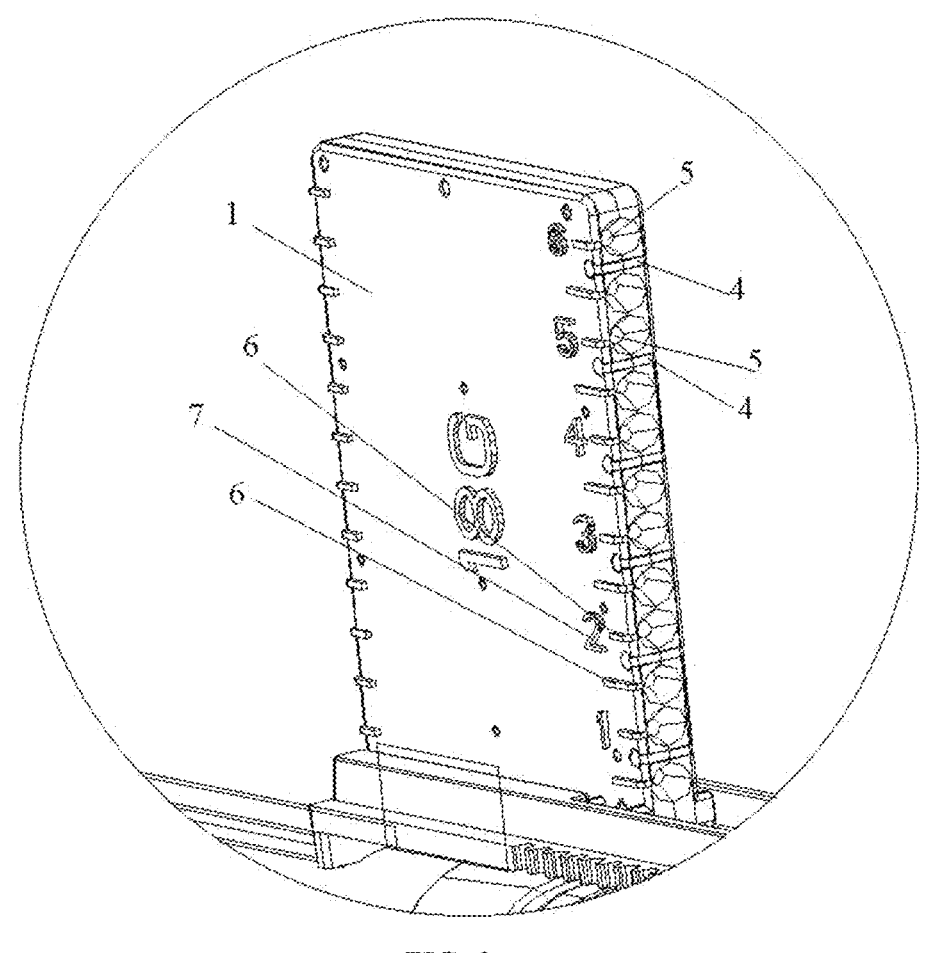
FIG. 3 is a schematic view of a puncture plate in an embodiment of the present disclosure.

The puncture plate has a plurality of puncture holes arranged at an equal interval. The puncture plate is fixedly installed on the ultrasonic probe by a biopsy puncture bracket. As shown in FIG. 3, the puncture plate is provided with a plurality of color bands 4 and a plurality of puncture holes 5, with all the puncture holes 5 arranged along in the same direction, and each color band 4 of the puncture plate 1 located between adjacent puncture holes 5. When performing the procedure, the operator can visually determine whether the puncture needle passes through a puncture hole on one side of the color band 4 or the other side of the color band 4, making it easier, more accurate, and time-efficient to identify the correct puncture hole, thereby improving surgical efficiency and reducing the risk of puncturing the wrong hole.

In particular, the puncture holes 5 on the puncture plate 1 are arranged vertically, making it easier to select different puncture positions. For example, two puncture holes 5 may be provided with one color band 4 between them. Alternatively, more than two puncture holes 5 may be provided, with a color band 4 provided between every adjacent two holes. In cases of providing a plurality of color bands 4, each band is of a color different from the others, making them easy to distinguish.

Furthermore, the puncture plate 1 is equipped with scale lines 6 corresponding to each puncture hole 5, and at least some of these scale lines are provided with numeral markers 7. These scale lines 6 and numeral markers 7 help operators accurately determine the puncture position, further improving surgical efficiency.

In an embodiment, in case that there are twelve puncture holes 5, twelve scale lines 6 are arranged corresponding to the puncture holes 5. Even-numbered scale lines 6 are labeled with numeral markers 7, and the numerical values of the numeral markers 7 increase from bottom to top, as such the structure is simple and easy to distinguish between the puncture holes 5.

Figure 4:
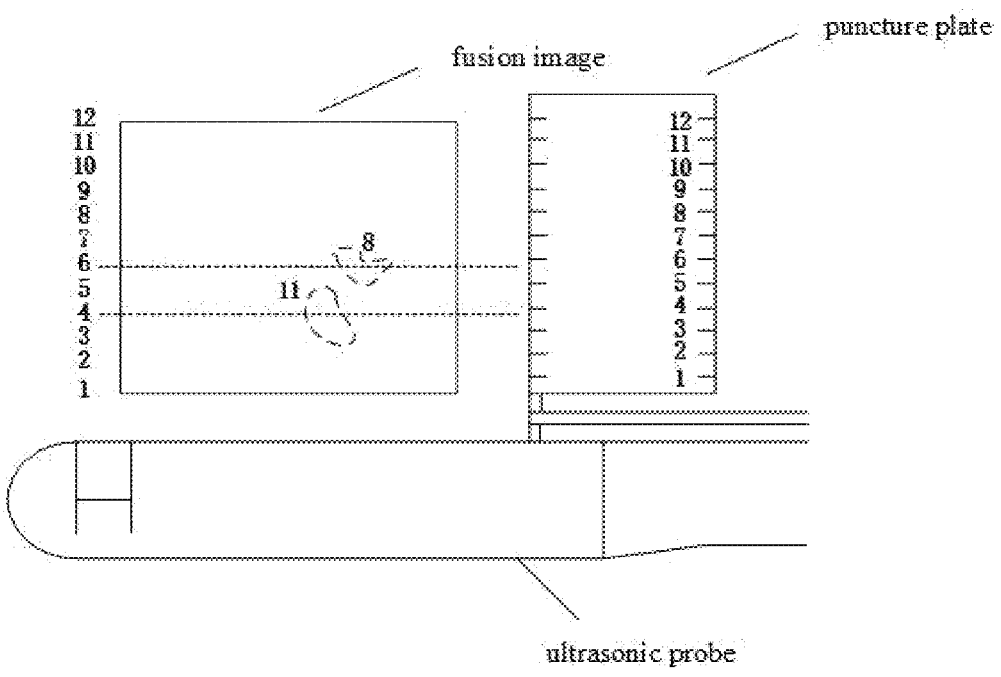
FIG. 4 is a schematic view of correlating prostate puncture markers with the puncture plate according to an embodiment of the present disclosure.

The target identifiers include at least one of the prostate puncture markers or the target area markers, all of which are ellipsoids with various volumes, shapes, and positions. When a scanning plane intersects a target identifier, the two-dimensional projection of the target identifier onto the scanning plane is obtained and displayed at the corresponding coordinate on the fusion image in the first display area. Two-dimensional imaging of the target identifier on the scanning plane is obtained. Based on the coordinate information of the two-dimensional imaging, and the actual positions of the puncture holes on the puncture plate, the correlation between the target identifier and the puncture holes is displayed in the fusion image in the second display area. As shown in FIG. 4, in an embodiment, the scanning plane intersects the prostate puncture markers 8 and 11. The coordinates of these prostate puncture markers 8 and 11 are calculated to obtain their corresponding puncture holes 6 and 4 on the puncture plate 1. Extending lines extending from respective puncture markers and directed to or passing through the corresponding puncture holes are displayed to show the correlation between the markers and the puncture holes. These extending lines guide the user to insert the puncture needle through the corresponding puncture holes 6 and 4, thus achieving sampling from the prostate puncture markers 8 and 11.

Figure 5:
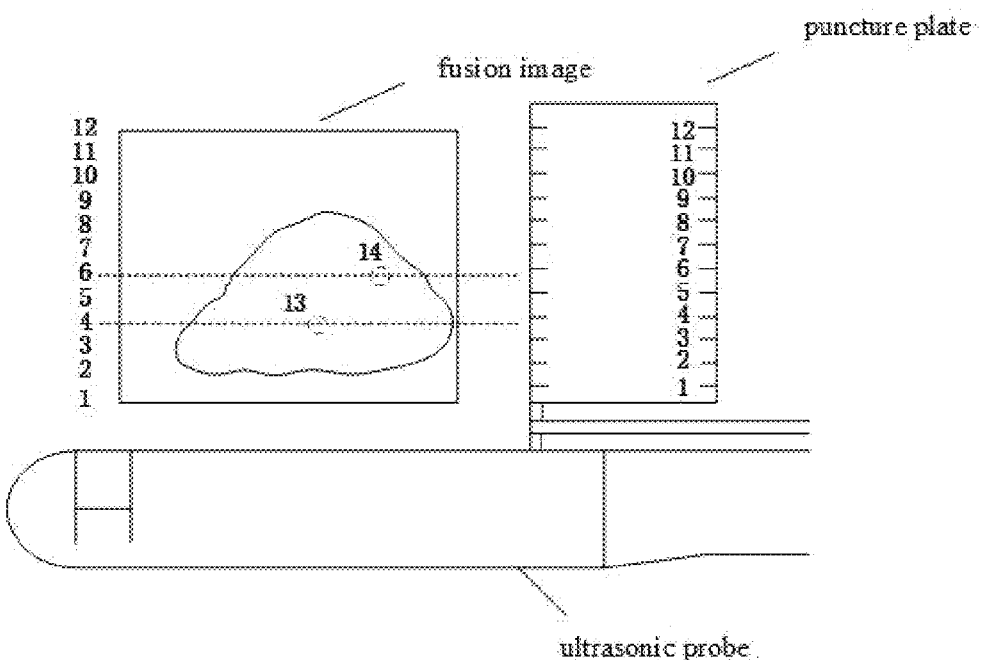
FIG. 5 is a schematic view of correlating target area markers with the puncture plate according to an embodiment of the present disclosure.

Referring to FIG. 5, when the scanning plane intersects the target area markers in the target identifier. Based on the area, coordinates, and other information of the two-dimensional imaging of the target area on the scanning plane, two additional cores 13 and 14 are generated which have fixed shapes and sizes in addition to 12 cores that have already been arranged. The corresponding puncture holes on the puncture plate are calculated, and their relationships are shown by extending lines extending from the puncture points and directed to or passing through the corresponding puncture holes. These extending lines guide medical personnel to insert the needle through puncture holes 6 and 4, achieving the sampling of the target area marker.

In the above solution, the position relationship between the ultrasonic probe model and the three-dimensional reconstruction model is dynamically and synchronously displayed in the first display area. In this way, through the first display area, the actual position relationship of ultrasonic probe and the prostate can be obtained in real time. Based on the scanning plan displayed on the ultrasonic probe model, it can control the scanning plane to accurately transect any target identifier on the three-dimensional reconstruction model, and then the fusion image of the ultrasound image and the section image, as well as the relationship between the target identifiers on the fusion image and the puncture holes on the puncture plate is displayed in the second display area. This assists the user in quickly and accurately performing a puncture sample using the corresponding puncture holes on the puncture plate, reducing sampling time, minimizing the number of samples, avoiding repeated punctures, lowering the operational threshold and learning curve for medical staff, while improving surgical experience of patients and reducing the probability of post-operative complications.

In an embodiment, the step of projecting at least one of the plurality of target identifiers onto the fusion image to obtain two-dimensional imaging of the at least one of the plurality of target identifiers comprises: acquiring first coordinate information of the at least one scanning plane and second coordinate information of the at least one of the plurality of target identifiers that intersects the at least one scanning plane; and projecting the at least one of the plurality of target identifiers onto the fusion image of the at least one scanning plane in two dimensions based on the first coordinate information and the second coordinate information.

An ultrasonic probe for prostate puncture surgery is typically a bi-window probe, which has two scanning planes that are perpendicular to each other. One window is located at the top of the ultrasonic probe and emits a fan-shaped detection area that is coplanar with the transverse plane. The other window is a rectangular, long-shaped probe positioned along the axis of the ultrasonic probe, emitting a rectangular detection area that is coplanar with the sagittal plane. As the probe units are fixed on the ultrasonic probe, the shapes and sizes of their scanning planes are fixed. By using the electromagnetic sensor installed at the tail of the ultrasonic probe collecting and simply calculating the electromagnetic coordinate information, the coordinate information of the scanning planes can be determined. Based on the coordinate information of each scanning plane and the three-dimensional coordinate information of the target identifier, the coordinates of the intersection between the target identifier and the scanning plane can be calculated. This allows the two-dimensional imaging of the target identifier on the scanning plane to be determined.

In one embodiment, the method further includes generating at least one prostate puncture marker within a two-dimensional projection of the target area marker in the fusion image.

Figure 6:
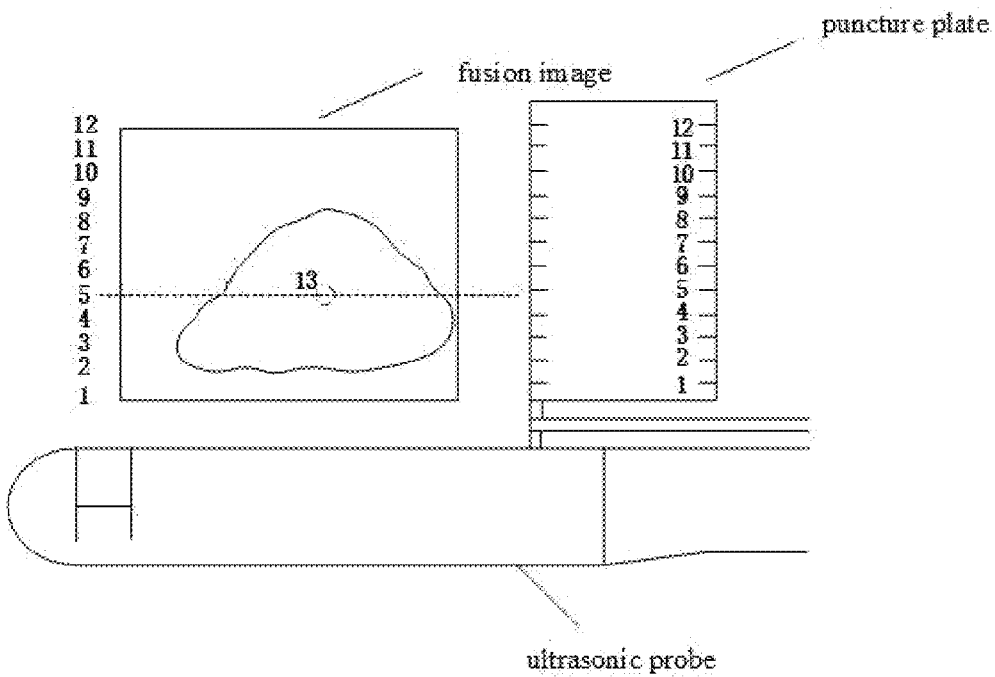
FIG. 6 is a schematic view of correlating the target area markers with the puncture plate according to another embodiment of the present disclosure.

Specifically, when the target identifier is a target area marker, the target area marker exists in the prostate structure of the three-dimensional reconstruction model in the form of an irregular ellipsoid. When there are a plurality of target area markers, there are a plurality of irregular ellipsoids of different volumes based on the sizes of the outlined target areas. The shapes of the ellipsoids are related to the shapes of the outlined target areas. Based on the coordinate information of each ellipsoid, the geometric center of each ellipsoid is calculated, and the coordinate of the geometric center is obtained. Referring to FIG. 6, when the target area marker is projected onto the fusion image in two dimensions, the geometric center is shown on the fusion image in the form of a regular circular prostate puncture marker 13, based on the coordinate information of the geometric center. The corresponding puncture hole on the puncture plate are calculated, and the relationship between the prostate puncture marker and the corresponding puncture hole is shown by the extending line, guiding medical personnel to perform the puncture and sample collection through the corresponding puncture hole. Since the prostate puncture marker represents the geometric center of the target area marker, the precision of sample extraction from within the target area marker is improved, avoiding repeated puncturing within the target area marker.

In one embodiment, the method further includes in response to a first operation, acquiring at least one target identifier selected by the first operation, that is followed by highlighting the at least one target identifier in the first display area; and/or hiding the at least one target identifier in the second display area.

Figure 7:
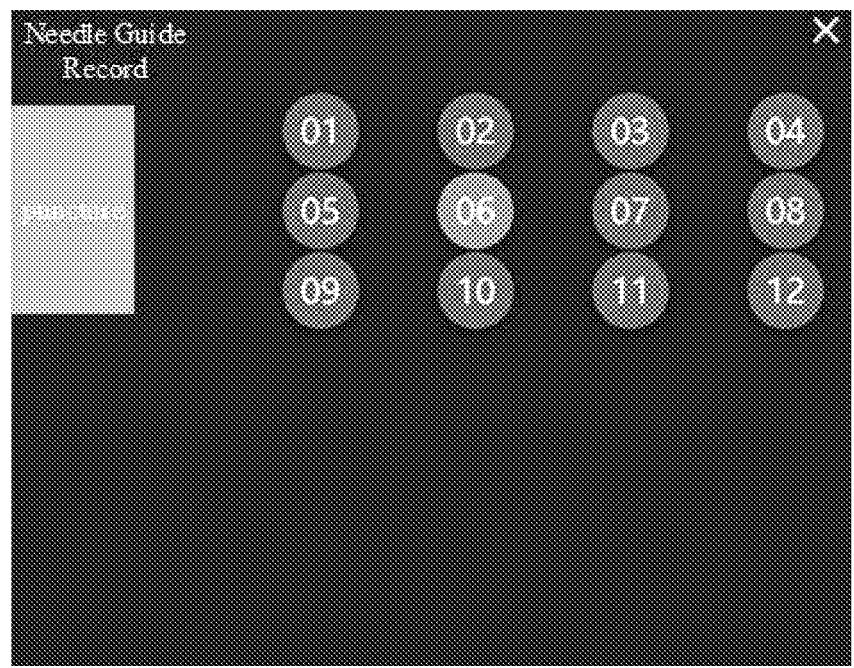
FIG. 7 is a schematic view illustrating selecting the prostate puncture markers according to an embodiment of the present disclosure.

The first operation may be a command input action performed by medical staff through an interactive device such as a touchscreen, keyboard, mouse, or other input devices. For example, as shown in FIG. 7, medical staff use the touchscreen to bring up an operation interface where each prostate puncture marker is identified by a numeral marker. By clicking on one or more numeral markers, the corresponding prostate puncture markers are selected. Based on the selected prostate puncture markers, the computer device sends relevant instructions to the display terminal, which controls the display terminal to highlight the selected prostate puncture marker in the first display area, while simultaneously displaying the corresponding numeral marker, and hides the selected prostate puncture marker in the second display area.

The above technical solution can be applied in various scenarios. When a particular prostate puncture marker has already been used for sampling or when it is not intended to be punctured, medical staff can select the puncture marker through the interactive device. The corresponding prostate puncture point is highlighted in the three-dimensional reconstruction model in the first display area, serving as tips information that this puncture point has been sampled, avoiding repeated puncturing. Further, in the second display area, or the fusion image, the puncture point can be hidden, along with its correlation relationship with the corresponding puncture hole, such as extending line indicators, to more effectively prevent medical personnel from performing repeated punctures.

Similarly, when the target identifier is a target area marker, similar operations can be performed to select the corresponding target area marker, thus avoiding puncture sampling of already punctured or unwanted target area markers.

In one embodiment, the method further includes displaying the at least one section image of the three-dimensional reconstruction corresponding to the at least one scanning plane in respective sub-display areas of a third display area.

In this embodiment, the first display area of the puncture guidance interface is used to display three-dimensional puncture guidance information, including the ultrasonic probe model and the three-dimensional reconstruction model. The second display area is used to display the fusion image, and two-dimensional puncture guidance information showing the relationship between the target identifier and the puncture plate. The third display area is used to solely display the section image of the current ultrasonic probe in the three-dimensional reconstruction model. This allows the user to intuitively view the section image of the current ultrasonic probe in the three-dimensional reconstruction model without interference from other factors. Moreover, by combining the information presented in the first and second display areas, puncture guidance information can be obtained from multi dimensions.

In this embodiment, the third display area further includes a first sub-area and a second sub-area, used to respectively display the section image corresponding to the first probe with the detection direction aligned with the transverse plane and the second probe with the detection direction aligned with the sagittal plane. This provides more comprehensive and multidimensional reference information for medical staff.

Figure 8:
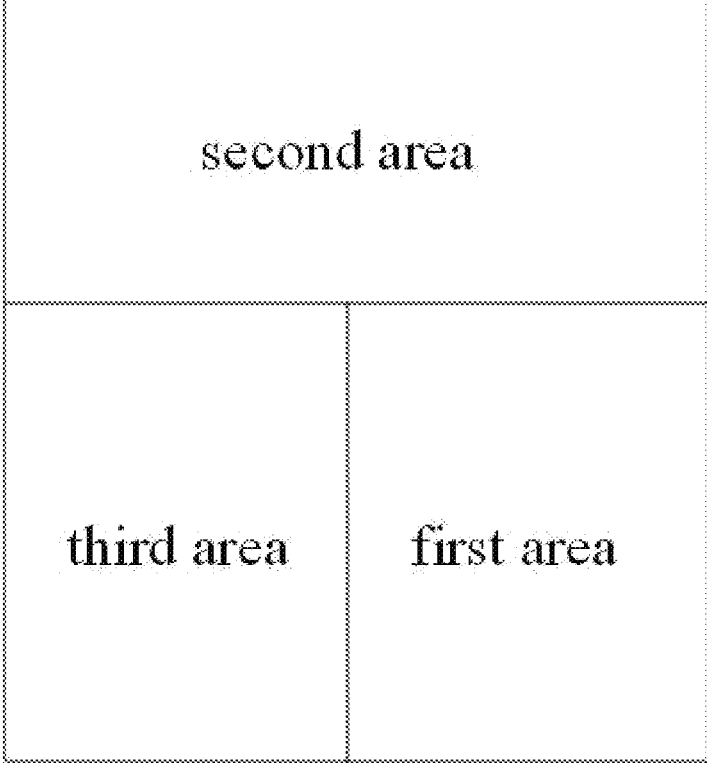
FIG. 8 is a schematic view of a layout of a puncture guidance interface according to an embodiment of the present disclosure.

In another embodiment, the layout of the puncture guidance interface is as shown in FIG. 8. It should be understood that the layout of the puncture guidance interface is not limited to the form shown in FIG. 8, and users can adjust the layout of the puncture guidance interface according to their preferences.

In one embodiment, the method further includes in response to a needle tip enhancement command, displaying at least one of a needle tip position of a sampling device and a safe puncture area in the fusion image based on a real-time coordinate of the sampling device.

A sampling device, typically a biopsy needle or other commonly used sample collection device, cuts through the target object by moving an outer needle and an inner needle asynchronously back and forth, leaving the sample from the target object in the slot of the inner needle. The sample is finally collected by removing the sample from the slot.

Figure 9:
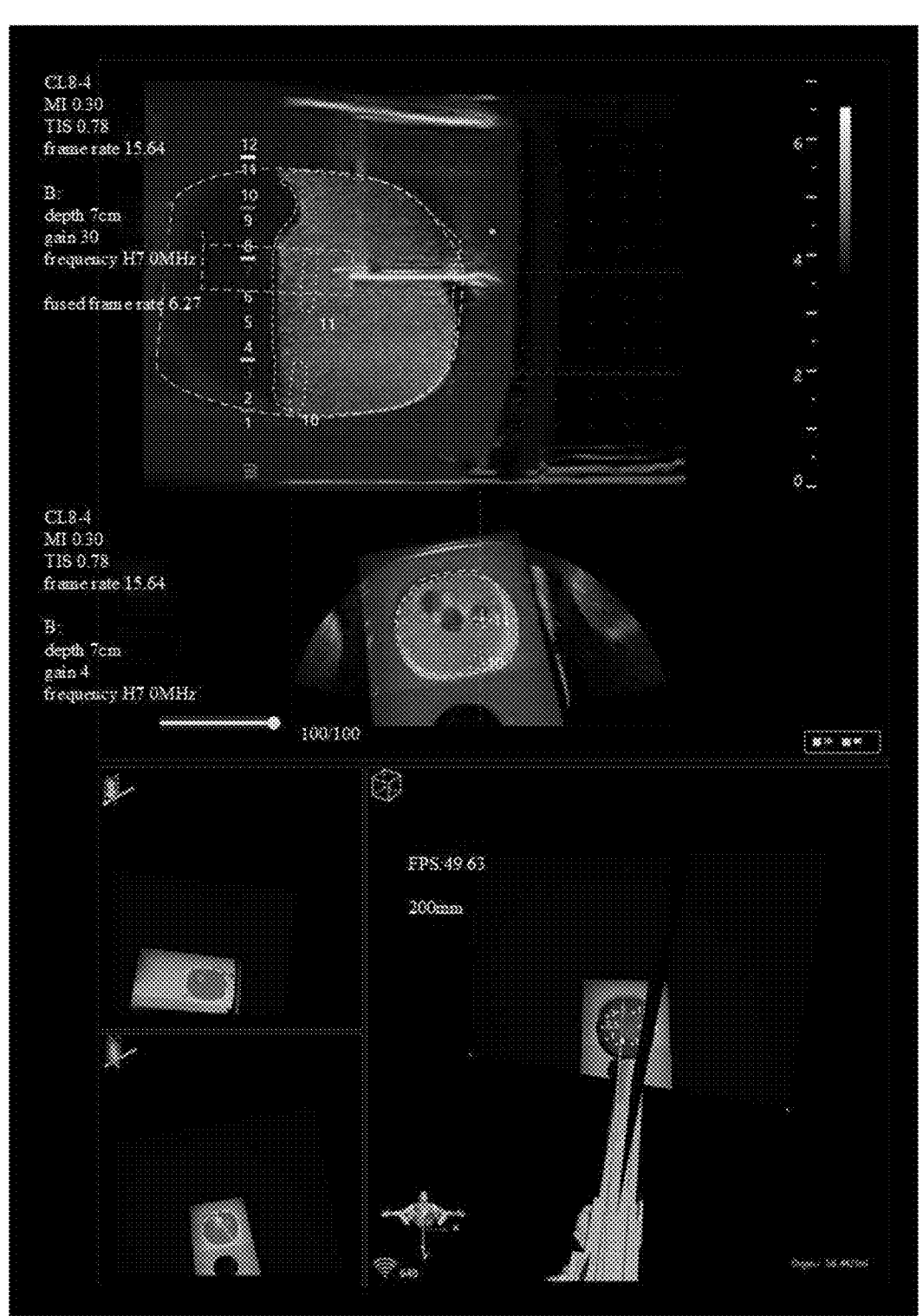
FIG. 9 is a schematic view of needle tip enhancement linked with a 3D model according to an embodiment of the present disclosure.

As shown in FIG. 9, the interactive terminal receives the needle tip enhancement command inputted by the user. Through the second display area, the real-time advancement of the puncture needle within the prostate can be observed, and the sensor mounted on the puncture needle collects real-time coordinate information. In this way, the needle tip position is displayed as a solid circle. Based on the needle tip position, a safe puncture zone (i.e., a rectangular dashed protective box) is calculated to assist medical staff in determining the needle insertion distance, enabling quick and precise needle insertion.

In this embodiment, by registering multi-modal medical images to convert the needle tip coordinate onto the ultrasound image, the ultrasound image is used for guiding precise punctures, further improving the accuracy of the puncture guidance. This can assist doctors in puncturing target markers, such as lesions or prostate puncture markers, more quickly, and further effectively reducing the puncture time and the possibility of postoperative complications.

In one embodiment, the method further includes displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters comprise at least one of contrast and transparency, and the identification parameters comprise outline colors.

In other words, to distinguish the ultrasound image and section image in the fusion image, they can be displayed with different transparency or contrast, facilitating the user to differentiate between them. In some embodiments, an interface is provided for adjusting display parameters, allowing users to adjust the display parameters of the ultrasound image and/or section image, thus enabling the display of the fusion image according to user needs, such as showing only the ultrasound image, only the section image, or a combination of both.

By identifying the prostate area in the ultrasound image and section image in the fusion image, it is possible to distinguish between the prostate areas of the two images. For example, as shown in FIG. 9, taking the MRI image as an example of the section image, the contour of the prostate area in the ultrasound image and the contour of the prostate area in the MRI image are displayed with dashed lines of different colors. Meanwhile, when the current scanning plane of the ultrasonic probe intersects the target marker, the corresponding two-dimensional imaging can be displayed, with the target area marker highlighted by a dashed line of one color and the prostate puncture marker points marked by a dashed line of another color and numeral markers. The contour shapes are determined by the outlined target markers and the cross-sectional angle. This enables medical staff to observe the puncture situation in real-time, such as the puncture angle and lesion location, and help doctors determine the correct puncture angle.

Figure 10:
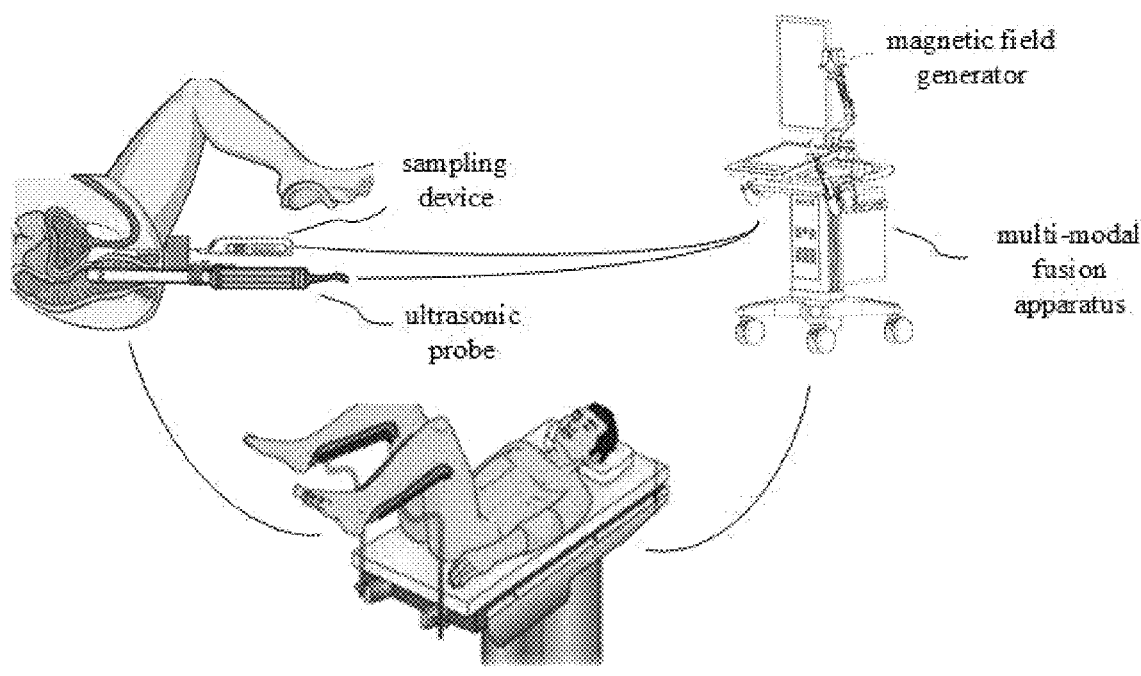
FIG. 10 is a schematic view of a specific application scenario of an embodiment of the present disclosure.

Referring to FIG. 10, in a specific application scenario, a patient undergoes prostate puncture guidance surgery. At this time, the patient lies flat on the operating table in a fixed position, with a multi-modal fusion apparatus placed beside them. This device integrates a magnetic field generator, electromagnetic sensors, an ultrasonic probe, a sampling device, a display terminal, and other equipment. The magnetic field generator is positioned above the left or right side of the patient and is used to emit a hemispherical magnetic field that covers the entire body of the patient. A first electromagnetic sensor is detachably fixed to the sampling device, and the first electromagnetic sensor has a first end connected to the sampling device and an opposite second end connected to the multi-modal fusion apparatus. A second electromagnetic sensor is detachably fixed to the ultrasonic probe, and the second electromagnetic sensor has a first end connected to the ultrasonic probe and a second end connected to the multi-modal fusion apparatus. When the sampling device and ultrasonic probe move within the magnetic field range, the electromagnetic sensors sense the corresponding coordinate and orientation information and return it to the multi-modal fusion apparatus. The MRI images of the patient prostate which are previously imported into the multi-modal fusion apparatus, have been registered through steps like registering and fusing, thereby registering two different coordinate systems of the MRI and ultrasound images. Based on the coordinate and orientation information returned by the electromagnetic sensors, the corresponding MRI image is extracted and displayed in fusion with the ultrasound image on the display of the multi-modal fusion apparatus, obtaining a fusion image. The display synchronously shows the three-dimensional prostate model of the patient. Medical staff can observe the relative position between the scanning plane of the ultrasonic probe and the three-dimensional prostate model. By rotating the ultrasonic probe, they can control the scanning plane to be tangent to the prostate puncture point or target area marker on the desired section of the three-dimensional prostate model. Afterward, the fusion image shows the guidance line of the prostate puncture point or target area marker to its specific puncture hole on the puncture plate. In a way such as the guidance line pointing to a corresponding hole number or the color of the guidance line matching and a color of a corresponding hole number, the specific puncture hole position is determined based on this guidance line. Then, medical staff operate the sampling device to puncture the specific hole for sampling. During the needle insertion process, the electromagnetic sensor mounted on the sampling device sends real-time coordinate information of the sampling device back to the multi-modal fusion apparatus. The multi-modal fusion apparatus calculates and displays the needle tip position in the fusion image and the safety puncture area based on the distance shown after stimulating the needle tip. By displaying the needle tip and the safety puncture area in real time, medical staff can track the trajectory of the needle tip within the patient prostate, correct any deviation promptly, and control the needle depth based on the safety puncture area, preventing damage to the patient prostate.

In the above application scenario, this technical solution can achieve rapid sampling, shorten the sampling time, reduce the number of needle insertions, avoid repeated punctures, lower the operational threshold and learning time for medical staff, and simultaneously improve surgical experience of the patient, reducing the probability of postoperative complications.

Figure 11:
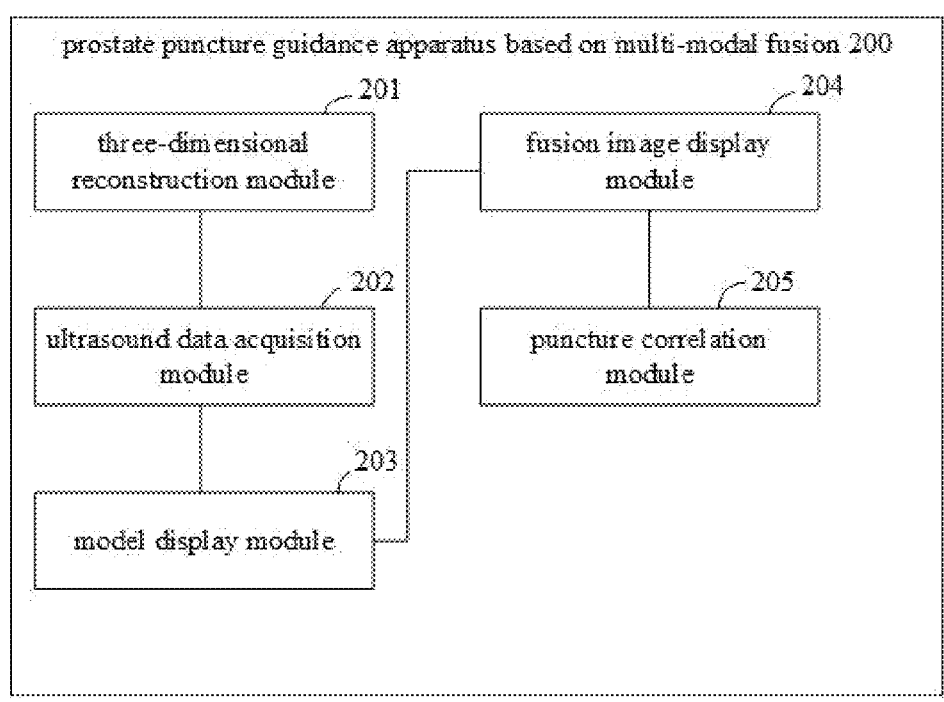
FIG. 11 is a schematic structural view of a prostate puncture guidance apparatus according to an embodiment of the present disclosure.

According to one or more embodiments of the present disclosure, as shown in FIG. 11, a prostate puncture guidance apparatus based on multi-modal fusion is provided, including:

a three-dimensional reconstruction module 201, configured for obtaining a medical image sequence of an object to be examined, and performing three-dimensional reconstruction based on the medical image sequence to obtain a three-dimensional reconstruction model of the object to be examined, wherein the three-dimensional reconstruction model comprises a prostate structure of the object to be examined, the prostate structure comprises a plurality of target identifiers, and the plurality of target identifiers comprise at least one of a prostate puncture marker and a target area marker;

an ultrasound data acquisition module 202, configured for obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner;

a model display module 203, configured for displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model;

a fusion image display module 204, configured for displaying a fusion image of the at least one section image of the three-dimensional reconstruction corresponding to the at least one scanning plane of the ultrasonic probe and the ultrasound image in a second display area; and projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and a puncture correlation module 205, configured for correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area.

The prostate puncture guidance apparatus based on multi-modal fusion is provided. The prostate model of the object to be examined and the ultrasonic probe model with at least one scanning plane are displayed in the same display area. Based on the real-time coordinate and ultrasound image information collected by the ultrasonic probe, the display area dynamically displays dynamic updates. Users may get the positional relationship between at least one scanning plane and the target identifier in the prostate model. This allows for quickly and accurately understanding the intersection between the scanning plane corresponding to the puncture plate installed on the ultrasonic probe and the target identifier. Additionally, through another display area showing the correlation between the specific puncture hole in the puncture plate and the target identifier, sampling can be quickly completed through the sampling device by penetrating the specific puncture hole. This reduces sampling time, decreases the number of punctures, avoids repeated punctures, lowers the operational level and learning time for medical staff, and enhances the surgical experience of patients.

In one embodiment, the fusion image display module 204 further configured for generating at least one prostate puncture marker within a two-dimensional projection of the target area marker in the fusion image.

In one embodiment, the fusion image display module 204 further configured for displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters comprise at least one of contrast and transparency, and the identification parameters comprise outline colors.

For specific details regarding the prostate puncture guidance apparatus based on multi-modal fusion, please refer to the previous definition of the prostate puncture guidance method based on multi-modal fusion, which will not be repeated here. Each module in the prostate puncture guidance apparatus based on multi-modal fusion can be implemented entirely or partially through software, hardware, or a combination of both. The modules can be embedded in or independent of the processor in computer device, or they can be stored as software in the memory of the computer device for easy access and execution by the processor.

Figure 12:
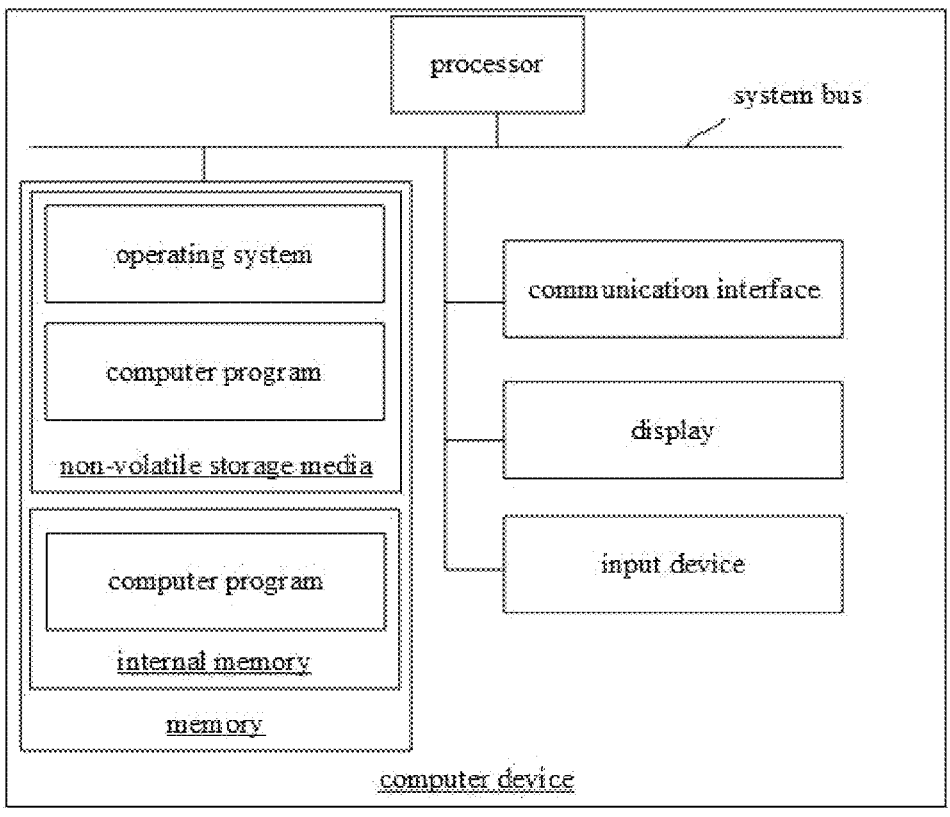
FIG. 12 is a schematic structural view of a computer device according to an embodiment of the present disclosure.

In one embodiment, a computer device is provided, which may be a user terminal. Its internal structure diagram is shown in FIG. 12. The computer device includes a processor, a memory, a communication interface, a display, and an input device which are connected via a system bus. The processor provides computational and control capabilities. The memory includes a non-volatile storage media and an internal memory. The non-volatile storage media stores the operating system and computer programs, while the internal memory provides an environment for the execution of the operating system and computer programs in the non-volatile storage media. The computer programs are executed by the processor to implement a prostate puncture guidance method based on multi-modal fusion. The communication interface is used for communication with external terminals via a network. The display can be an LCD or e-ink screen. The input device of the computer device can be a touch layer covering the display, buttons, trackball, or touchpad on the computer outer covering, or an external keyboard, touchpad, or mouse.

Those skilled in the art will understand that the structure shown in FIG. 12 is just a block diagram of part of the structure related to the present disclosure and does not limit the computer device to which the disclosure is applied. The specific computer device may include more or fewer components than shown in the diagram, or some components may be combined, or the components may have a different arrangement.

In one embodiment, the prostate puncture guidance apparatus based on multi-modal fusion provided by the present disclosure can be implemented as a computer program, which can run on the computer device as shown in FIG. 12. The memory of the computer device can store various program modules that make up the prostate puncture guidance apparatus based on multi-modal fusion, such as the three-dimensional reconstruction module, the ultrasound data acquisition module, the model display module, the fusion image display module, and the puncture correlation module, as shown in FIG. 11. The computer program formed by these program modules enables the processor to execute the steps of the prostate puncture guidance method based on multi-modal fusion described in various embodiments of the present disclosure. For example, the computer device shown in FIG. 12 can perform Step 201 through the three-dimensional reconstruction module, Step 202 through the ultrasound data acquisition module, Step 203 through the model display module, Step 204 through the fusion image display module in the prostate puncture guidance apparatus based on multi-modal fusion, and so on.

Accordingly, in one embodiment, a computer device is provided, including a memory and a processor. The memory stores a computer program. When the processor executes the computer program, the prostate puncture guidance apparatus based on multi-modal fusion provided by any embodiment of the present disclosure is implemented.

Those skilled in the art will understand that the entire or partial processes of the methods in the above embodiments can be completed by instructing the relevant hardware through a computer program. The program can be stored in a non-volatile computer-readable storage medium, and when executed, it can include the processes from the embodiments of the methods mentioned above.

In the embodiments provided by the present disclosure, any reference to memory, storage, databases, or other media may include both non-volatile and/or volatile memories. Non-internal memory may include read-only memory (ROM), programmable ROM (PROM), electrically programmable ROM (EPROM), electrically erasable programmable ROM (EEPROM), or flash memory. internal memory may include random access memory (RAM) or external cache memory. As an illustration rather than a limitation, RAM includes various forms, such as static RAM (SRAM), dynamic RAM (DRAM), synchronous DRAM (SDRAM), double data rate SDRAM (DDR SDRAM), enhanced SDRAM (ESDRAM), synchronous link DRAM (SL-DRAM), Rambus direct RAM (RDRAM), direct memory access DRAM (DRDRAM), and memory bus dynamic RAM (RDRAM), etc.

The technical features of the above embodiments can be combined in any way. For the sake of simplicity, not all possible combinations of the technical features in the above embodiments are described. However, as long as the combinations of these technical features do not contradict each other, they should be considered within the scope of the description in this document.

The embodiments described above express only a portion of the implementation methods of the present disclosure. The description is specific and detailed, but should not be construed as limiting the patent scope of the disclosure. It should be noted that, for those skilled in the art, several modifications and improvements can be made without departing from the concepts of the present disclosure, all of which fall within the protection scope of the present disclosure.

What is claimed is:

1. A prostate puncture guidance method based on multi-modal fusion, comprising steps of:

obtaining a medical image sequence of an object to be examined, and performing three-dimensional reconstruction based on the medical image sequence to obtain a three-dimensional reconstruction model of the object to be examined, wherein the three-dimensional reconstruction model comprises a prostate structure of the object to be examined, the prostate structure comprises a plurality of target identifiers, and the plurality of target identifiers comprise at least one of a prostate puncture marker and a target area marker;

obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner;

displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model;

displaying a fusion image of the at least one section image of the three-dimensional reconstruction corresponding to the at least one scanning plane of the ultrasonic probe and the ultrasound image in a second display area;

projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area, wherein the step of projecting at least one of the plurality of target identifiers onto the fusion image to obtain two-dimensional imaging of the at least one of the plurality of target identifiers comprises:

acquiring first coordinate information of the at least one scanning plane and second coordinate information of the at least one of the plurality of target identifiers that intersects the at least one scanning plane; and projecting the at least one of the plurality of target identifiers onto the fusion image of the at least one scanning plane in two dimensions based on the first coordinate information and the second coordinate information, wherein the puncture plate is provided with a plurality of puncture holes, and wherein the step of correlating the two-dimensional imaging of the at least one of the plurality of target identifiers with at least one corresponding puncture hole of the puncture plate installed on the ultrasonic probe, and displaying a correlation relationship between the two-dimensional imaging of the at least one of the plurality of target identifiers and the at least one corresponding puncture hole in the second display area comprises:

calculating to determine the at least one corresponding puncture hole corresponding to the at least one of the plurality of target identifiers which intersects the at least one scanning plane according to the second coordinate information, displaying the plurality of puncture holes in the second display area, and displaying at least one extending line extending from the at least one corresponding puncture hole and passing through the at least one of the plurality of target identifiers corresponding to the at least one corresponding puncture hole in the second display area to show the correlation relationship between the two-dimensional imaging of the at least one of the plurality of target identifiers and the at least one corresponding puncture hole.

2. The prostate puncture guidance method according to claim 1, further comprising:

generating at least one prostate puncture marker within a two-dimensional projection of the target area marker in the fusion image.

3. The prostate puncture guidance method according to claim 1, further comprising:

in response to a first operation, acquiring at least one target identifier selected by the first operation, that is followed by highlighting the at least one target identifier in the first display area; and/or hiding the at least one target identifier in the second display area.

4. The prostate puncture guidance method according to claim 1, further comprising:

displaying the at least one section image of the three-dimensional reconstruction corresponding to the at least one scanning plane in respective sub-display areas of a third display area.

5. The prostate puncture guidance method according to claim 1, further comprising:

in response to a needle tip enhancement command, displaying at least one of a needle tip position of a sampling device and a safe puncture area in the fusion image based on a real-time coordinate of the sampling device.

6. The prostate puncture guidance method according to claim 1, further comprising:

displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters comprise at least one of contrast and transparency, and the identification parameters comprise outline colors.

7. A prostate puncture guidance apparatus based on multimodal fusion, comprising:

a three-dimensional reconstruction module, configured for obtaining a medical image sequence of an object to be examined, and performing three-dimensional reconstruction based on the medical image sequence to obtain a three-dimensional reconstruction model of the object to be examined, wherein the three-dimensional reconstruction model comprises a prostate structure of the object to be examined, the prostate structure comprises a plurality of target identifiers, and the plurality of target identifiers comprise at least one of a prostate puncture marker and a target area marker;

an ultrasound data acquisition module, configured for obtaining a real-time coordinate of an ultrasonic probe and an ultrasound image of the object to be examined, and obtaining at least one section image of the three-dimensional reconstruction model based on the real-time coordinate, the at least one section image being corresponding to at least one scanning plane of the ultrasonic probe in a one-to-one correspondence manner;

a model display module, configured for displaying the three-dimensional reconstruction model in a first display area, displaying an ultrasonic probe model of the ultrasonic probe based on the real-time coordinate, and displaying the at least one section image of the three-dimensional reconstruction corresponding to the at least one scanning plane of the ultrasonic probe in at least one detection region of the ultrasonic probe model;

a fusion image display module, configured for displaying a fusion image of the at least one section image of the three-dimensional reconstruction corresponding to the at least one scanning plane of the ultrasonic probe and the ultrasound image in a second display area; and projecting at least one of the plurality of target identifiers onto the fusion image to obtain two-dimensional imaging of the at least one of the plurality of target identifiers when the at least one scanning plane intersects the at least one of the plurality of target identifiers in the three-dimensional reconstruction model; and a puncture correlation module, configured for correlating the two-dimensional imaging of the at least one of the plurality of target identifiers with at least one corresponding puncture hole of a puncture plate installed on the ultrasonic probe, and displaying a correlation relationship between the two-dimensional imaging of the at least one of the plurality of target identifiers and the at least one corresponding puncture hole in the second display area, wherein the fusion image display module is further configured for:

acquiring first coordinate information of the at least one scanning plane and second coordinate information of the at least one of the plurality of target identifiers that intersects the at least one scanning plane; and projecting the at least one of the plurality of target identifiers onto the fusion image of the at least one scanning plane in two dimensions based on the first coordinate information and the second coordinate information, wherein the puncture plate is provided with a plurality of puncture holes, and wherein the puncture correlation module is further configured for:

calculating to determine the at least one corresponding puncture hole corresponding to the at least one of the plurality of target identifiers which intersects the at least one scanning plane according to the second coordinate information, displaying the plurality of puncture holes in the second display area, and displaying at least one extending line extending from the at least one corresponding puncture hole and passing through the at least one of the plurality of target identifiers corresponding to the at least one corresponding puncture hole in the second display area to show the correlation relationship between the two-dimensional imaging of the at least one of the plurality of target identifiers and the at least one corresponding puncture hole.

8. The prostate puncture guidance apparatus based on multi-modal fusion according to claim 7, further configured for generating at least one prostate puncture marker within a two-dimensional projection of the target area marker in the fusion image.

9. The prostate puncture guidance apparatus based on multi-modal fusion according to claim 7, further configured for:

in response to a first operation, acquiring at least one target identifier selected by the first operation, that is followed by highlighting the at least one target identifier in the first display area; and/or hiding the at least one target identifier in the second display area.

10. The prostate puncture guidance apparatus based on multi-modal fusion according to claim 7, further configured for displaying the at least one section image of the three-dimensional reconstruction corresponding to the at least one scanning plane in respective sub-display areas of a third display area.

11. The prostate puncture guidance apparatus based on multi-modal fusion according to claim 7, further configured for displaying at least one of a needle tip position of a sampling device and a safe puncture area in the fusion image based on a real-time coordinate of the sampling device, in response to a needle tip enhancement command.

12. The prostate puncture guidance apparatus based on multi-modal fusion according to claim 7, further configured for:

displaying the ultrasound image and the at least one section image of the three-dimensional reconstruction corresponding to the at least one scanning plane of the ultrasonic probe with different display parameters; and/or marking a prostate contour of the ultrasound image and a prostate contour of the at least one section image of the three-dimensional reconstruction corresponding to the at least one scanning plane of the ultrasonic probe in the fusion image with different identification parameters, wherein the display parameters comprise at least one of contrast and transparency, and the identification parameters comprise outline colors.

13. A computer device, comprising a memory and a processor, wherein the memory stores a computer program, and when the computer program is executed by the processor, the method according to claim 1 is implemented.

14. A computer device, comprising a memory and a processor, wherein the memory stores a computer program, and when the computer program is executed by the processor, the method according to claim 2 is implemented.

15. A prostate puncture guidance system based on multi-modal fusion, comprising a magnetic field generator, a first electromagnetic sensor, a second electromagnetic sensor, an ultrasonic probe, a puncture plate, a sampling device, a display terminal and the computer device according to claim 13, wherein the ultrasonic probe is equipped with the puncture plate, the ultrasonic probe is provided with the first electromagnetic sensor, the sampling device is provided with the second electromagnetic sensor, and the magnetic field generator, the display terminal, the ultrasonic probe and the electromagnetic sensors are respectively in communication connection with the computer device.

16. A prostate puncture guidance system based on multi-modal fusion, comprising a magnetic field generator, a first electromagnetic sensor, a second electromagnetic sensor, an ultrasonic probe, a puncture plate, a sampling device, a display terminal and the computer device according to claim 14, wherein the ultrasonic probe is equipped with the puncture plate, the ultrasonic probe is provided with the first electromagnetic sensor, the sampling device is provided with the second electromagnetic sensor, and the magnetic field generator, the display terminal, the ultrasonic probe and the electromagnetic sensors are respectively in communication connection with the computer device.

\* \* \* \* \*